US00PP15517P2

(12) United States Plant Patent
van Delft

(10) Patent No.: US PP15,517 P2
(45) Date of Patent: Feb. 1, 2005

(54) ***PYRACANTHA* PLANT NAMED 'CADVAR'**

(50) Latin Name: *Pyracantha hybrida*
Varietal Denomination: Cadvar

(75) Inventor: M. Peter van Delft, Marldon (GB)

(73) Assignee: Agri Obtentions S.A., Guyancourt Cedex (FR)

( * ) Notice: Subject to any disclaimer, the term of this patent is extended or adjusted under 35 U.S.C. 154(b) by 0 days.

(21) Appl. No.: 10/636,596

(22) Filed: Aug. 8, 2003

(51) Int. Cl.[7] ..... A01H 5/00
(52) U.S. Cl. ..... Plt./253
(58) Field of Search ..... Plt./253

*Primary Examiner*—Kent Bell
(74) *Attorney, Agent, or Firm*—Burns, Doane, Swecker & Mathis, L.L.P.

(57) ABSTRACT

A new and distinct white-flowered *Pyracantha* plant is provided that is a spontaneous whole plant mutation of the 'Cadrou' cultivar (non-patented in the United States). The new cultivar readily forms white flowers and red berries and can be readily distinguished from the 'Cadrou' cultivar by presence of attractive variegated leaves. A broad-bushy to flat-bushy growth habit with robustness and abundant branching commonly is displayed. Good resistance to scab and fire blight is provided to the grower. During observations to date less fructification than the 'Cadrou' cultivar has been noted.

2 Drawing Sheets

Botanical/commercial classification: *Pyracantha hybrida*/*Pyracantha* Plant.
Varietal denomination: cv. 'Cadvar'.

SUMMARY OF THE INVENTION

A new and distinct cultivar of the *Pyracantha* plant is provided that is a spontaneous whole plant mutation of unknown causation of the 'Cadrou' cultivar (non-patented in the United States). The new cultivar was discovered during 1997 in cultivated area while growing among plants of the 'Cadrou' cultivar at Devon, United Kingdom. Had the new cultivar of the present invention not been discovered and carefully preserved, it would have been lost to mankind.

The new cultivar was selected and preserved primarily because of the distinctive atypical appearance of the foliage.

It was found that the new cultivar of the present invention possesses the following combination of characteristics:

(a) forms attractive variegated foliage unlike the 'Cadrou' cultivar, (b) forms white flowers and red berries commonly with less abundant fructification than the 'Cadrou' cultivar, (c) displays good resistance to scab and fire blight, and (d) commonly exhibits a broad-bushy to flat-bushy growth habit with robustness and abundant branching.

The new cultivar of the present invention well meets the needs of the horticultural industry and is particularly well suited for growing as attractive ornamentation in the landscape.

The new cultivar can be readily distinguished from the 'Cadrou' cultivar in view of the variegated foliage. Also, during observations to date the fructification of the new cultivar has been considerably less than that of the 'Cadrou' cultivar.

The new cultivar has been found to readily undergo asexual propagation by the use of cuttings. Roots readily are produced from such cuttings during the summer. Such asexual propagation has been carried out at Devon, United Kingdom, and at West Grove, Pa., U.S.A., and has shown that the new cultivar reproduces true to type in subsequent generations.

The new cultivar has been named the 'Cadvar'.

BRIEF DESCRIPTION OF THE PHOTOGRAPHS

The accompanying photographs show four year-old plants of the new cultivar while growing during the summer at La Ménitré, France. Such plants had been asexually reproduced by the rooting of cuttings.

DETAILED DESCRIPTION

Figure 1:
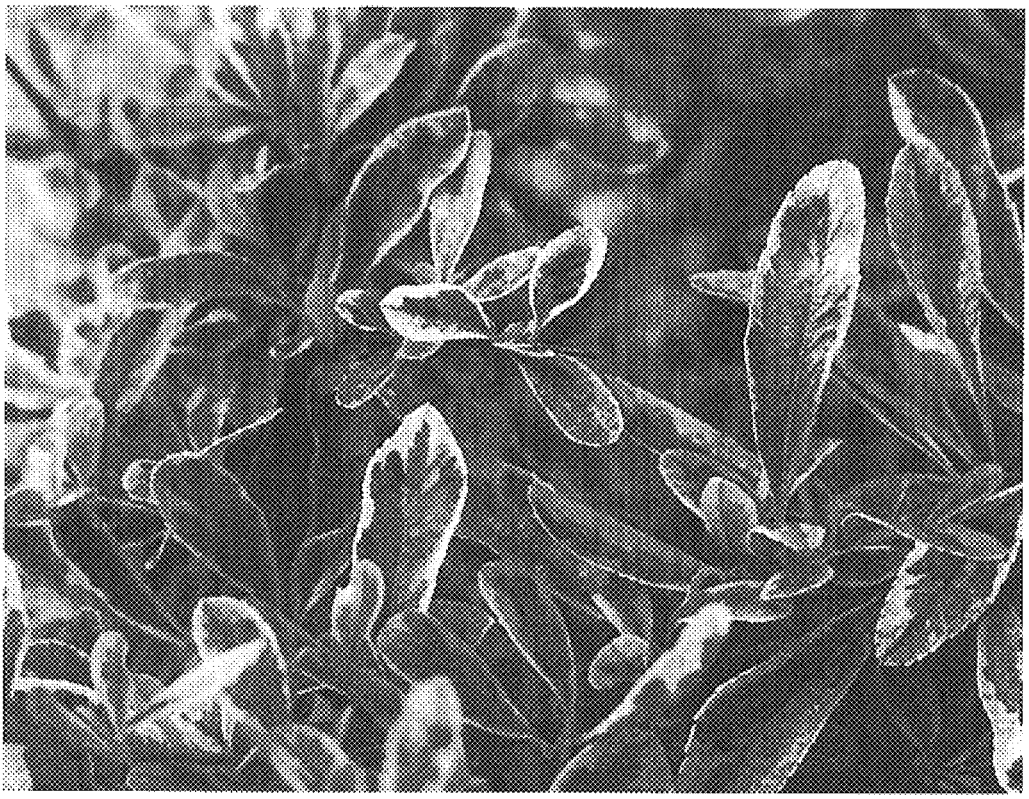
FIG. 1 shows a close view of the attractive variegated foliage. Such variegation is absent in the foliage of the 'Cadrou' parental cultivar.
Figure 2:
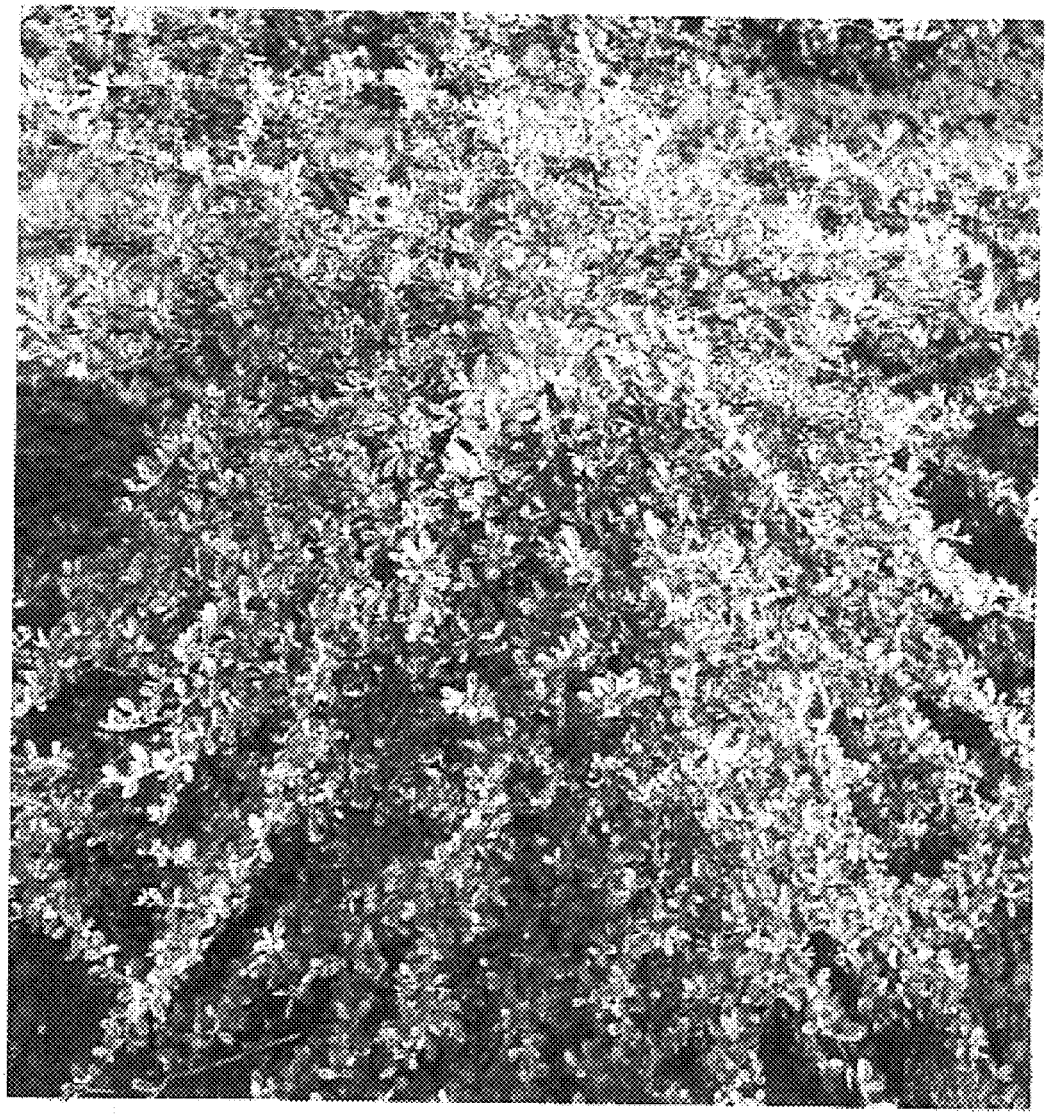
FIG. 2 illustrates the typical growth habit and abundant branching of the new cultivar.

The following description is based on the observation of three year-old plants of the new cultivar while growing outdoors at West Grove, Pa., U.S.A. The blooms were observed on Jun. 19, 2003. Other characteristics were observed on Jun. 12, 2003. The plants had been asexually reproduced by the rooting of cuttings. Color designations are with reference to The R.H.S. Colour Chart of The Royal Horticultural Society London, England. When employed common color terms are to be accorded their customary dictionary significance.

Origin: A spontaneous mutation of unknown causation of the 'Cadrou' cultivar (non-patented in the United States).

Plant:

*Habit.*—Young plants commonly are broad-bushy to flat-bushy. However, when tied to a stake the plant will assume an upright growth habit.

*Size.*—Commonly rounded, and approximately 80 cm in height and diameter with the size being influenced by the climatic conditions that are experienced.

Branches:

*Color.*—Young stems: When exposed to the sun, the tip of current season growth commonly is from near Greyed-Purple Group 183A to near Greyed-Orange Group 176B and 176C. At the base where shaded, the presence of purple pigment diminishes and approaches Greyed-Orange Group 176B and 176C to predominantly Yellow-Green Group 146C and 147C in the direction of the tip. The most mature portions of the current season stems are near Greyed-Purple Group 187A when exposed to the sun and near Yellow-Green Group 146C when shaded. Adult stems: predominantly Greyed-Green Group 197A and 197B commonly with some Greyed-Green Group 191A.

*Texture.*—Densely covered with fine silvery pubescence.

*Size.*—Approximately 14.5 cm in length on average, and approximately 3 mm in diameter on average.

*Internode length.*—Approximately 6 mm on average.

Thorns:

*General appearance.*—Numerous, sharply pointed, approximately 1.5 to 2.5 cm in length, approximately 1 to 2 mm in width at the base, and near Brown Group 200B in coloration.

Foliage:

*Leaf general appearance.*—Nicely variegated with slight glossiness.

*Leaf length.*—Commonly approximately 12 to 41.25 mm.

*Leaf width.*—Commonly approximately 4 to 12.75 mm.

*Leaf bearing.*—Alternate and simple.

*Leaf shape.*—Variable, narrowly elliptic to oblanceolate to obovate, occasionally spatulate, and rarely laceolate.

*Leaf base.*—Attenuate to narrowly cuneate.

*Leaf apex.*—Broadly acute to obtuse.

*Leaf margin.*—Closely crenulate serrulate.

*Leaf texture.*—Glabrescens, and becoming glabrous with a few scattered hairs commonly remaining on mature leaves.

*Leaf color.*—New foliage: upper surface: at the center in admixture near Green Group 138A, 138B, and 138C, and at the margin in an irregular pattern near Yellow-Green Group 145B and near Yellow Group 4C. Under surface: at the center near Greyed-Green Group 191B, and at the margin in an irregular pattern near Yellow-Green Group 145C and near Yellow Group 4C. Mature foliage: Upper surface: at the center in admixture near Green Group 137C and 138A and small amounts of near Green Group 139D, and at the margin in an irregular pattern near Yellow-Green Group 145A, 145B, 145C, and 154D. Under surface: at the center near Greyed-Green Group 191B, and at the margin in an irregular pattern near Yellow-Green Group 145C.

*Stipules.*—Very small, commonly present in pairs, and commonly approximately 1 to 1.5 mm in length. The minute size precludes further characterization when viewed in the absence of magnification.

*Petioles.*—Commonly approximately 2.5 to 4.5 mm in length, approximately 0.4 to 0.6 mm in width, with a wide groove on the upper surface, commonly possess a few scattered hairs on the upper surface, substantially glabrous on the under surface, and Yellow-Green Group 145A in coloration on the upper surface, and Yellow-Green Group 145B on the under surface.

Inflorescence:

*Number.*—Approximately 1000 flowers per plant during the time of blooming and considerably less than the 'Cadrou' cultivar during observations to date.

*Time of blooming.*—Commonly mid- to late-spring.

*Duration of blooming.*—Commonly approximately 10 to 14 days on average.

*Buds.*—Globose, approximately 3 mm in length, approximately 2 mm in diameter at the widest point, and near Yellow-Green Group 145D in coloration.

*Size.*—A fully open inflorescence commonly measures approximately 10 to 11 mm in diameter on average, and approximately 3 mm in depth on average.

*Configuration.*—Flattened when fully open.

*Petal number.*—Five.

*Petal arrangement.*—Radial.

*Overall petal shape.*—Rounded.

*Petal apex.*—Obtuse.

*Petal base.*—Obtuse.

*Petal margin.*—Entire.

*Petal length.*—Commonly approximately 3.7 mm on average.

*Petal width.*—Commonly approximately 4.5 mm on average.

*Color.*—Near White Group 155D on both surfaces.

*Fragrance.*—Lightly musty.

*Lastingness of an inflorescence.*—Approximately 4 to 7 days on the plant depending upon the environmental conditions.

*Sepals.*—Six in number, minute and too small to measure, and near Yellow-Green Group 145D in coloration on both surfaces.

*Stamens.*—Approximately 10 on average and attached to the petals.

*Pollen.*—Present in a moderate quantity.

*Anthers.*—Near White Group 155D in coloration.

*Filaments.*—Near White Group 155D in coloration.

*Pistils.*—Four per inflorescence on average.

*Berries.*—Rarely formed, flattened in configuration when rarely present and near Red Group 46B. The fructification is considerably less than that of the 'Cadrou' parental cultivar during observations to date.

The disease resistance of the new cultivar is believed to be comparable to that of the 'Cadrou' parental cultivar. Good resistance to scab [*Spilocaea pyracanthae* (Otth.) Rostrup] and fire blight [*Erwinia amylovora* (Burr.) Winsl. et al.] has been observed.

Plants of the 'Cadvar' cultivar have well withstood a temperature as low as 3° F. during observations to date. Accordingly, considerable hardiness can be attributed to the new cultivar.

Plants of the new 'Cadvar' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Pyracantha* plant that is a spontaneous whole plant mutation of the 'Cadrou' cultivar having the following combination of characteristics:

(a) forms attractive variegated foliage unlike the 'Cadrou' cultivar, (b) forms white flowers and red berries commonly with less fructification than the 'Cadrou' cultivar, (c) displays good resistance to scab and fire blight, and (d) commonly exhibits a broad-bushy to flat-bushy growth habit with robustness and abundant branching;

substantially as illustrated and described.

* * * * *